US009950118B2

(12) United States Patent
Kjeldsen et al.

(10) Patent No.: US 9,950,118 B2
(45) Date of Patent: Apr. 24, 2018

(54) MEDICAL INJECTION DEVICE COMPRISING A SECONDARY SAFETY LIMITER

(71) Applicant: Novo Nordisk A/S, Bagsvaerd (DK)

(72) Inventors: Bastian G. Kjeldsen, Hilleroed (DK); Brian Mouridsen, Fredensborg (DK); Jim Radmer, Fredensborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 707 days.

(21) Appl. No.: 14/395,716

(22) PCT Filed: Mar. 15, 2013

(86) PCT No.: PCT/EP2013/055452
§ 371 (c)(1),
(2) Date: Oct. 20, 2014

(87) PCT Pub. No.: WO2013/156226
PCT Pub. Date: Oct. 24, 2013

(65) Prior Publication Data

US 2015/0105732 A1 Apr. 16, 2015

Related U.S. Application Data

(60) Provisional application No. 61/638,565, filed on Apr. 26, 2012, provisional application No. 61/638,766, filed on Apr. 26, 2012.

(30) Foreign Application Priority Data

Apr. 20, 2012 (EP) .................................... 12165081
Apr. 20, 2012 (EP) .................................... 12165082

(51) Int. Cl.
*A61M 5/315* (2006.01)
*A61M 5/20* (2006.01)
*A61M 5/24* (2006.01)

(52) U.S. Cl.
CPC .......... *A61M 5/31501* (2013.01); *A61M 5/20* (2013.01); *A61M 5/3155* (2013.01);
(Continued)

(58) Field of Classification Search
CPC .......... A61M 5/31501; A61M 5/31541; A61M 5/31583; A61M 5/3155; A61M 5/31535;
(Continued)

(56) References Cited

U.S. PATENT DOCUMENTS 9,375,534 B2 * 6/2016 Veasey .................... A61M 5/24
2006/0116647 A1 6/2006 Geiser et al.
(Continued)

FOREIGN PATENT DOCUMENTS

EP 2644217 A1 * 10/2013 .............. A61M 5/20
JP H07194701 A 8/1995
(Continued)

*Primary Examiner* — Lauren P Farrar
(74) *Attorney, Agent, or Firm* — Wesley Nicolas

(57) ABSTRACT

The present invention relates to an injection device (1) for setting and injecting set doses from a held drug cartridge (10). The injection device (1) comprises a housing (110,120, 130, 140), a piston rod (800), a rotatable driver (500, 700) and a dose setting device (400). The dose setting device (400) comprises a predetermined stop to limit the amount of an expelled dose corresponding to the amount of a set dose. A secondary stop limiter includes first (700) and second (270) components and a secondary stop track follower (950) arranged between the first (700) and second (270) components. If the predetermined stop fails to stop the driver (500, 700) at the end of injection, the secondary stop track follower (950) moves towards a safety stop (708) to prevent the driver (500, 700) from rotating further.

15 Claims, 10 Drawing Sheets

(52) U.S. Cl.
CPC .... *A61M 5/31535* (2013.01); *A61M 5/31541* (2013.01); *A61M 5/31553* (2013.01); *A61M 5/31583* (2013.01); *A61M 5/31585* (2013.01); *A61M 5/3157* (2013.01); *A61M 5/31593* (2013.01); *A61M 2005/2026* (2013.01); *A61M 2005/2407* (2013.01); *A61M 2005/2492* (2013.01); *A61M 2005/3154* (2013.01); *A61M 2005/31518* (2013.01); *F04C 2270/0421* (2013.01)

(58) Field of Classification Search
CPC ................ A61M 5/20; A61M 5/31553; A61M 5/31585; A61M 2005/3154; A61M 2005/31518; A61M 2005/2407; A61M 2005/2492; A61M 5/3157; A61M 5/31593; A61M 2005/2026; F04C 2270/0421
See application file for complete search history.

(56) References Cited

U.S. PATENT DOCUMENTS

| | | | | |
|---|---|---|---|---|
| 2007/0073236 | A1 | 3/2007 | Mernoe et al. | |
| 2015/0018772 | A1 * | 1/2015 | Schenker ................ | A61M 5/20 604/189 |
| 2015/0065963 | A1 | 3/2015 | Kjeldsen et al. | |

FOREIGN PATENT DOCUMENTS

| | | | |
|---|---|---|---|
| JP | 2010503434 | A | 2/2010 |
| JP | 2010104797 | A | 5/2010 |
| WO | 98/10814 | A1 | 3/1998 |
| WO | 06105792 | A1 | 10/2006 |
| WO | 2006105792 | A1 | 10/2006 |
| WO | 2007017053 | A1 | 2/2007 |
| WO | 2010070038 | A2 | 6/2010 |
| WO | 2010125153 | A1 | 11/2010 |
| WO | 11045611 | A2 | 4/2011 |
| WO | 2011045611 | A2 | 4/2011 |

* cited by examiner

MEDICAL INJECTION DEVICE COMPRISING A SECONDARY SAFETY LIMITER

CROSS-REFERENCE TO RELATED APPLICATIONS

This application is a 35 U.S.C. § 371 National Stage application of International Application PCT/EP2013/055452 (published as WO 2013/156226), filed Mar. 15, 2013, which claimed priority of European Patent Application 12165082.4, filed Apr. 20, 2012, and European Patent Application 12165081.6, filed Apr. 20, 2012; this application claims priority under 35 U.S.C. § 119 of U.S. Provisional Application 61/638,565; filed Apr. 26, 2012, and U.S. Provisional Application 61/638,766; filed Apr. 26, 2012.

The present invention generally relates to medical injection devices adapted for managing medical therapy. In particular, the invention relates to medical injection devices adapted to provide ease of use in a cost-effective way.

BACKGROUND OF THE INVENTION

In the disclosure of the present invention reference is mostly made to the treatment of diabetes by delivery of insulin, however, this is only a an exemplary use of the present invention.

Conventional delivery devices for delivery of liquid drugs by means of subcutaneous injection typically have been provided as devices such as pen-shaped devices having a cylindrical form-factor. The cylindrical form-factor approach has mainly been chosen due to the particular use of cylindrical drug-filled cartridges. While the cylindrical form-factor generally enables design of slim devices, this form-factor typically has short-comings as regards device length and available surface area for presenting information to the user, e.g. by means of a display.

To overcome these problems, delivery devices having form-factors other than the pen-shaped form-factor have been proposed. Examples of injection devices having both the cylindrical form-factor as well as devices having a non-cylindrical form factor are disclosed in WO 98/10814.

Generally, from a users viewpoint there is a wish that the delivery device is as slim and short as possible in order to provide for a compact device which may be easily carried about, i.e. in a shirt-pocket or the like. At the same time, there is a wish that modern injection devices offer an increasingly variety of features. Such features may include a large display for presenting the size of the set dose, a large maximum dosing amount available for each single administration, automatic expelling of set doses, the prevention of setting a dose exceeding the drug amount remaining in the device, etc.

In a recent publication, WO 2011/045611 discloses a spring driven injector having a dose setting arrangement to select a dose volume and a drive mechanism which in some forms include a preloaded spring having stored energy sufficient to expel the entire useable contents of a cartridge over a succession of doses. In accordance with the teachings of WO 2011/045611 the proposed injection devices presents drawbacks having regard to building length. In addition, the proposed window arrangement for indicating set doses provides a far from user friendly design as it includes a window that rotates relative to the housing as the dose is being dialled. Furthermore, potentially unsafe situations may occur if a mechanical defect should occur within the device causing an uncontrolled expelling of the entire contents of the cartridge.

WO 2007/017053 discloses a syringe device that comprises a dose limiting mechanism to prevent ejection of a dose exceeding a set dose and a safety mechanism that prevents ejection of a dose exceeding the set dose in case the dose limiting mechanism should fail.

Having regard to the above discussion, it is a first object of the present invention to provide a medical injection device that is safer in use compared to prior art injection devices.

It is a further object of the present invention to provide an injection device that includes a secondary safety mechanism that enables more flexibility in the design than in prior art devices.

It is a further object of the present invention to provide an injection device that is more compact than prior art devices.

It is a still further object of the present invention to provide an injection device that is superior in user friendliness compared to prior art devices.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first aspect of the invention an injection device for setting and injecting set doses from a held drug cartridge is provided. The injection device comprises:

- a housing defining proximal and distal ends,
- a dose setting arrangement including a dose setting device that is moved in a first direction away from a predetermined stop in accordance with the size of a set dose and that moves back to the predetermined stop during injection of the set dose, the predetermined stop being configured for being fixedly arranged relative to the housing,
- a piston rod adapted to translate relative to the housing, in a distal direction in order to expel a set dose,
- a driver coupled to the piston rod, the driver being adapted to rotate during dose injection to cause the piston rod to translate relative to the housing, and
- a mechanism adapted for coupling rotational movement of the dose setting device with rotational movement of the driver such that the driver exclusively rotates when the dose setting device moves back towards the predetermined stop during injection of the set dose, The injection device further defines:
- a first component that rotates around a first axis as the driver rotates during injection but remains rotationally fixed relative to the housing during dose setting, the first component having a first track disposed thereon,
- a second component that is arranged coaxially with the first component for rotation around the first axis, wherein the second component rotates as the dose setting device rotates during dose setting and wherein the second component is rotatably fixed relative to the housing during dose injection, the second component having a second track disposed thereon, and
- a secondary stop track follower arranged between the first component and the second component, the secondary stop track follower being in engagement with the first track and in engagement with the second track, wherein the first track and the second track are configured to cause the secondary stop track follower to move along the first axis when the first component and the second component rotate relative to each other, and wherein, if the predetermined stop fails to stop the driver at the end of injection, the secondary stop track follower moves towards a safety stop to prevent the driver from rotating further.

In accordance herewith, an improved injection device with a secondary safety stop is provided which provides an increase in safety of operation. In case the primary limitation function associated with the dose setting device fails, or in case a clutch arrangement within the device fails, the secondary stop function will prevent the injection device from running loose.

Compared to prior art injection devices, the invention provides a faster responding safety system that will be better synchronized with the predetermined stop associated with the dose setting device that is intended to limit dose movements at the end of the dose expelling movement. Further the invention provides for increased flexibility for designing the safety system due to the fact that the secondary safety stop mechanism may be positioned at a location where it does not take up space required by other components.

In particular where the secondary safety stop is coupled to a component other than the piston rod, i.e. where the secondary stop track follower does not engage the piston rod, the lead of the one more threads of the secondary safety stop may differ from the lead of the piston rod providing increased opportunities for designing the secondary stop function with superior operability.

In some embodiments one of the first track and the second track is shaped to form a thread whereas the other one of the first track and the second track forms an axial track.

In other embodiments both the first track and second track form threads wherein the lead of the first track is different than the lead of the second track.

At least one of the first track and the second track forms a thread wherein the safety stop is arranged fixedly relative to the at least one thread.

In accordance with the first aspect, the first component is a component separate from the piston rod. In some embodiments the driver defines the first component.

The safety stop may be provided as a rotational stop surface adapted to abut a rotational stop surface provided on the secondary stop track follower to prevent further rotation of the first component beyond the safety stop.

The injection device may include a dosage selector coupled to the dose setting device for operating the dose setting device and an injection activator adapted to be activated to inject the set dose.

In further embodiments, the injection device defines a first clutch arrangement arranged between the dose setting device and the second component wherein the first clutch arrangement is engaged during dose setting so that the second component rotates as the dose setting device rotates, and wherein the first clutch arrangement is disengaged during dose injection to enable the dose setting device to rotate independently of the second component.

Also, the injection device may define a second clutch arrangement arranged between the first component and the housing wherein the second clutch arrangement is engaged during dose setting so that the first component is prevented from rotating during dose setting, and wherein the second clutch arrangement is disengaged during dose injection to enable the first component to rotate relative to the housing.

The piston rod may be formed as a flexible piston rod having a first end extending along the first axis and adapted to engage a piston of a held cartridge and wherein the second end of the piston rod is adapted to be flexed away from the first axis. The flexible piston rod may be provided as a series of interconnected links or alternatively as an incompressible helical spring. In still other embodiments, the piston rod is formed by a rigid rod shaped member.

As commonly known for injection devices, the piston rod may include one or more threads or alternatively a single axially extending track in combination with a single thread, where each track or thread is engaging respective corresponding geometries in the drive nut and a guide member fixedly arranged relative to the drug cartridge.

The injection device may further comprise a stored energy source, the stored energy source being configured to drive rotation of the driver when the injection activator is activated.

The stored energy source may comprise energy sufficient to drive the piston rod for expelling the entire useable contents of drug contained in the cartridge. The stored energy source may be provided as a spring device wherein the spring device may be tensed already during manufacture so that the user is not required to provide energy to the spring device prior to activation of the injection activator for expelling a set dose. The spring device may for example be provided as a constant force spring. In particular embodiments, the spring device is provided as a constant force spring having a first end that is would around an axis a) and a second end that is wound around another axis b) that is offset relative to said axis a) by a certain distance.

Examples of spring devices include an s-shaped constant force spring. Such spring device may be arranged in an s-shaped configuration where the first end is wound around the axis of the dose control member and the second end is wound around the axis of the cartridge.

At least a piston engaging end of the piston rod may extend along the first axis, wherein the driver defines a drive nut that rotates around the first axis and wherein the dose setting device is adapted to rotate around a second axis, the second axis being offset from the first axis by a distance and wherein the driver further defines a drive member rotatable around the second axis, the drive member being coupled to the drive nut so that the drive nut rotates as the drive member rotates.

In alternative embodiments the longitudinal axis of a held cartridge defines a second axis, the second axis being offset from the first axis by a distance, wherein the driver defines a drive nut that rotates around the second axis and wherein the driver further defines a drive member rotatable around the first axis, the drive member being coupled to the drive nut so that the drive nut rotates as the drive member rotates wherein the dose setting device is adapted to rotate around the first axis, and wherein said first component is a component that rotates as the drive member rotates. In such a device, the said second component and the secondary stop track follower are configured for rotation around the first axis.

The housing of the medical device may be so shaped and sized as to allow it to be held in a hand of the user and easily carried in a pocket.

Thus, in a second aspect of the invention a medical injection device for setting and injecting set doses from a held drug cartridge is provided, where the medial injection device comprises:

a housing, a dose setting arrangement including a dose setting device that is moved in a first direction away from a predetermined stop in accordance with the size of a set dose and that moves back to the predetermined stop during injection of the set dose, the predetermined stop being configured for being fixedly arranged relative to the housing, an injection activator adapted to be activated to inject the set dose, a piston rod adapted to translate relative to the housing in a distal direction in order to expel a set dose, a rotatable driver coupled to the piston rod and including a stored energy source configured to drive rotation of the driver when the injection activator is activated to cause the piston rod to translate relative to the housing, wherein:

the dose setting device defines a dose control member configured for rotation around a second axis, a first clutch arrangement arranged between the dose control member and the driver, wherein the first clutch arrangement is disengaged during dose setting so that the dose control member rotates independently of the driver, and wherein the first clutch arrangement engages upon activation of the injection activator to enable the driver to rotate the dose control member while causing the dose setting device to move back towards the predetermined stop, and a second clutch arrangement arranged between the driver and the housing, wherein the second clutch arrangement is engaged during dose setting so that the driver is prevented from rotating during dose setting, and wherein the second clutch arrangement disengages upon activation of the injection activator to enable the driver to rotate relative to the housing.

In accordance herewith, an improved injection device is provided which due to the configuration of the first and the second clutch arrangements offers increased flexibility in the structural design of the device, ultimately allowing a more compact device to be provided. In addition, the design enables the dose setting arrangement to include a dose setting device that moves relative to the housing of the device both during dose setting as well as during injection of a set dose. In accordance herewith, the dose setting device may include a dose indicator that may be viewed through a window either formed in the housing or otherwise associated with the housing at a location that is rotationally fixed relative to the housing.

The dose setting device will typically be provided as a component that defines a minimum dose setting and a maximum dose setting and wherein a current position of the dose setting device between the minimum dose setting and the maximum dose setting, when the injection device is shifted from a dose setting mode to a dose expelling mode, defines the amount that is expelled during expelling of a set dose. The dose setting arrangement may be so configured that doses can be dialled up and dialled down so that an initially set dose can be dialled down without causing drug to be expelled from the device.

The dose setting device of the dose setting arrangement may in some embodiments comprise or be provided as a component that rotates relative to the housing, such component being formed as a cylindrical member or alternatively a disc shaped member. A disc shaped member may be arranged as a rigid member or otherwise as a flexible member such as a member made of foil. In still other embodiments, the dose setting device is a component that is displaced linearly without rotation. In some forms the component is formed as a mechanical dial having a series of dose indicia formed along the length of travel of the component. For a cylindrical member, such member may include a thread that engages a thread associated or formed in the housing and wherein a series of dose indicia is formed along a helical path arranged in accordance with the lead of the thread. Alternatively to forming the dose setting device as a dial, a dial may be provided as a device that is separate from the dose setting device.

In particular forms, the dose setting device rotates in unison with the rotational movements of the dose control member, optionally allowing for relative axial movements (i.e. movements parallel to the second axis) between the two components. In other embodiments, a gearing is provided between the rotational movements of the dose control member and the dose setting device. In still other embodiments, the dose setting device is formed by the dose control member itself.

Typically, the drug cartridge for use with the injection device may be provided in the form of a cylindrical cartridge having a piston movable in a distal direction towards an expelling end of the cartridge, where the expelling end of the cartridge is sealed by a penetrable septum adapted to be pierced by a subcutaneous injection needle.

In some embodiments of the injection device the driver defines a drive member arranged for rotation coaxially with the dose control member. In such configuration, the drive member may be provided with a first track disposed thereon while the dose control member may be provided with a second track. An end of content track follower is arranged between the drive member and the dose control member where the end of content track follower is in engagement both with the first track and the second track to follow each of the tracks. The first track and the second track are configured to cause the end of content track follower to move along the second axis when the dose control member is rotated relative to the drive member. The end of content track follower moves towards an end of content stop as the dose setting device is dialled up, the end of content stop being arranged at a predefined position to prevent the dose setting device from being rotated beyond a dose setting corresponding to the end of track follower engaging the end of content stop.

Hence, an end of content feature may be provided to prevent a user from dialling up a dose of a size exceeding the useable content of drug remaining in the cartridge. The end of content stop may be associated with the first track or the second track, for example by forming an end stop at the end of the respective track, i.e. on the drive member or the dose control member. At least one of the first and the second tracks forms a thread wherein the end of content stop is arranged fixedly relative to the at least one thread. The end of content stop may be provided as a rotational stop to ensure a well-defined stop limitation position.

The first clutch arrangement may be so configured that during dose injection the first clutch arrangement prevents the drive member from rotating relative to the dose control member. Hence, during injection, the end of track follower will maintain its position relative the engaging tracks and hence also relative to the end of content stop.

In some embodiments one of the first and the second tracks forms a thread whereas the other one of the first and the second track forms an axial track. In other embodiments both the first and the second tracks forms threads and wherein the lead of the first track is different than the lead of the second track. Hence, the end of content track follower will be forced to move in an axial direction as the dose control member moves relative to the drive member during dose setting.

The dose control member may be axially moveable back and forth relative to the housing, e.g. between a default or inactivated proximal position and an activated distal position. The dose control member may be biased towards the inactivated position by a spring element. In some embodiments the dose control member defines an injection activator which may form an injection button. In some embodiments, the dose control member is moved from the inactivated position and into an activated position responsive to an injection button being operated to inject the set dose. The injection button may be connected to the dose control member so that these two components are fixed relative to each other with respect to axial movements. The injection button and the dose control member may be arranged to allow relative rotational movements.

In particular embodiments, the expelling of a set dose may be halted at any time by releasing finger pressure exerted on the injection button. When pressure is released the dose control member is automatically moved into its proximal position due to the bias provided by spring element. Hence, in such situation, the second clutch arrangement re-engages which thus prevents the drive member from rotating. However, expelling of the remaining part of the set dose may be continued by renewed pressing down the injection button.

In particular embodiments, the dose control member operates the first clutch arrangement and the second clutch arrangement. When the dose control member is in the inactivated position the first clutch arrangement disengages the coupling between the dose control member and the driver while the second clutch arrangement locks the driver against rotational movement relative to the housing. When the dose control member is in the activated position the first clutch arrangement couples rotational movement between the dose control member and the driver while the second clutch arrangement unlocks the driver with respect to rotational movements relative to the housing.

In some forms the injection device comprises a dose setting member coupled to the dose setting device for operating the dose setting device, e.g. so that the dose setting device rotates as the dose setting member rotates. The dose control member may interconnect the dose setting member and the dose setting device.

The dose setting member may be configured to be manually gripped by the hand of the user for dialling up and dialling down the dose to be injected. In other forms, a separate dosage selector is coupled to the dose setting member so that the dose setting member is rotated as the dosage selector is manipulated by the hand of the user. In such forms, the dosage selector may be provided as an endless band that is coupled to the dose setting member so that movement of flexible band is transformed into a rotation of the dose setting member.

A third clutch arrangement may be arranged between the dose control member and the dose setting member, wherein the third clutch arrangement is engaged during dose setting so that the dose control member rotates together with the dose setting member, and wherein the third clutch arrangement disengages upon activation of the injection activator to enable the dose control member to rotate independently from the dose setting member.

Also, a fourth clutch arrangement may be provided which controls the rotation of the dose setting member relative to the housing so that when the injection activator is in the inactivated position the rotation of the dose setting member is enabled whereas when the injection activator is in the activated position rotation of the dose setting member is prevented.

The dose control member may in some embodiments be configured to operate either one or both of the third and fourth clutch arrangements, i.e. in correspondence with the axial position of the dose control member. Hence, in particular embodiments the dose control member may control the first, the second, the third and the fourth clutch arrangements. In accordance herewith, safe control of the device is provided with a large degree of control of the components of the device during dose setting mode as well as during dose expelling mode.

In different further embodiments, the various features according to the first aspect are combined with one or more features according to the second aspect.

As used herein, the term “drug” is meant to encompass any drug-containing flowable medicine capable of being passed through a delivery means such as a hollow needle in a controlled manner, such as a liquid, solution, gel or fine suspension. Further, “drug” is meant also to encompass mediums for nasal or pulmonary administration. Representative drugs include pharmaceuticals such as peptides, proteins, and hormones, biologically derived or active agents, hormonal and gene based agents, nutritional formulas and other substances in both solid (dispensed) or liquid form. In the description of the exemplary embodiments reference will be made to the use of insulin. Correspondingly, the terms “subcutaneous” and “transcutaneous” injection or infusion is meant to encompass any method of transcutaneous delivery to a subject.

BRIEF DESCRIPTION OF THE DRAWINGS

In the following the invention will be further described with references to the drawings, wherein.

DESCRIPTION OF EXEMPLARY EMBODIMENTS

The shown figures are schematic representations for which reason the configuration of the different structures as well as the relative dimensions are intended to serve illustrative purposes only.

Figure 1:
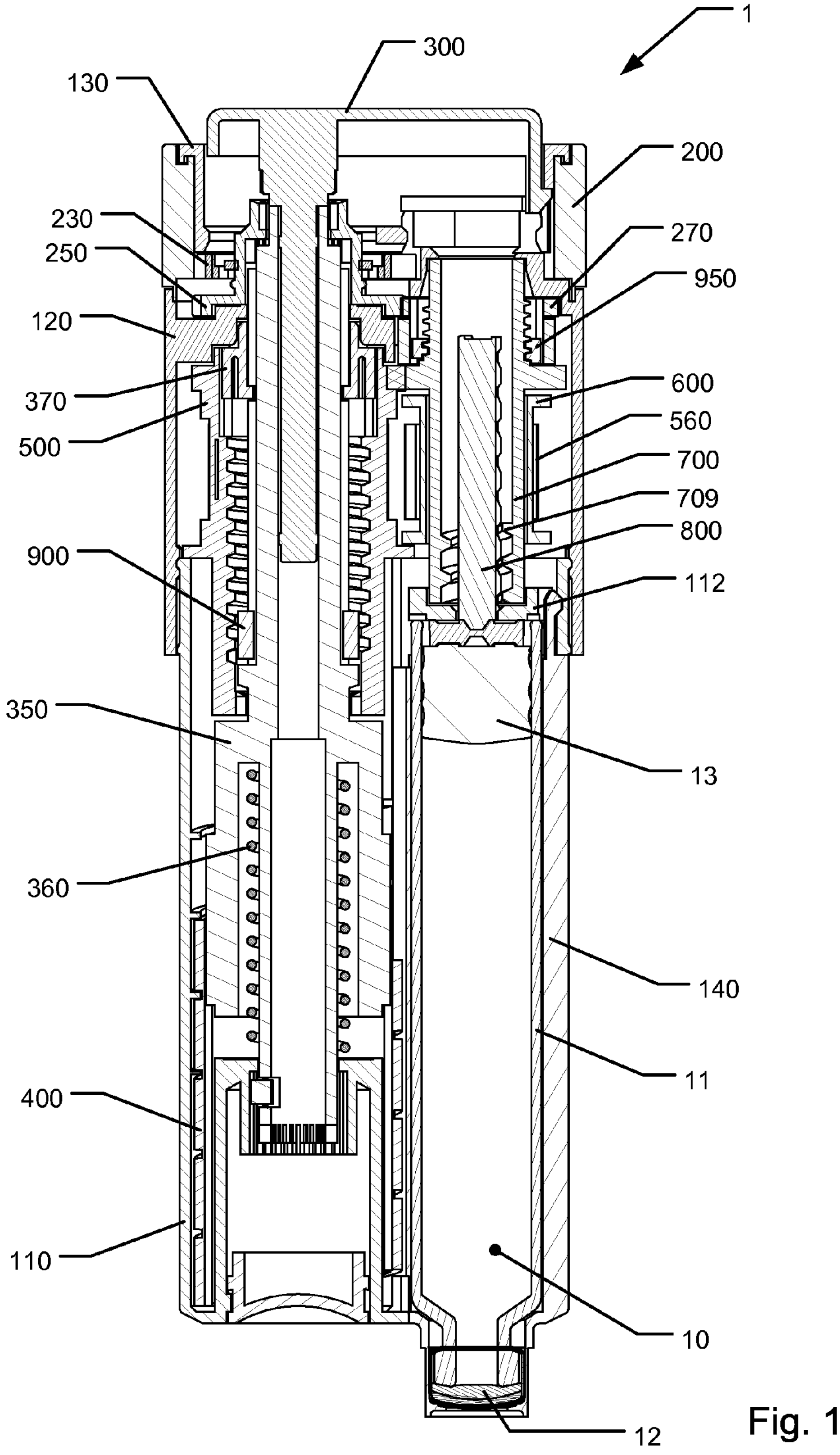
FIG. 1 shows a cross sectional side view of an embodiment of a medical injection device 1 in accordance with the invention.

In the context of the following discussion it may be convenient to define that the term "distal end" in the appended figures is meant to refer to the end of the injection device which usually carries the injection needle whereas the term "proximal end" is meant to refer to the opposite end pointing away from the injection needle, i.e. the end carrying an injection button as depicted in FIG. 1. The term "axial" refers to directions parallel with a central longitudinal axis of a held cylindrical drug cartridge.

FIG. 1 shows a cross sectional side view of an embodiment of an injection device 1 for use by a patient for medical self-treatment, the injection device 1 being configured for repetitively setting and injecting individually set doses of a drug. The injection device 1 includes a housing (110,120, 130,140) which along a main axis defines an elongated structure and which at least along a part of its length, in a direction transverse to the main axis, is formed with a non-cylindrical cross section exhibiting a somewhat flat shape, such a device being generally referred to as a "closer" device.

The injection device 1 is shown as a cartridge-based injection device wherein a drug filled cartridge 10 is accommodated within the housing (110,120,130,140). The cartridge 10 has an elongated body 11 and a pierceable septum 12 covering a distal outlet end of the body 11 for cooperation with a replaceable subcutaneous injection needle (not shown). Also, cartridge 10 includes a piston 13 mounted within body 11 for sliding movement along an expelling axis of the cartridge. In FIG. 1 the expelling axis lies in the plane of the cross section. When a needle assembly (not shown) is mounted on the cartridge 10, piston 13 may be forced in the distal direction along the expelling axis for expelling portions of the drug accommodated in the cartridge. Either the cartridge 10 or the housing (110,120,130,140) defines a needle mount adapted to releasably mount a needle assembly, e.g. a double pointed injection needle. The injection device 1 shown in FIG. 1 may further include a cap (not shown) which detachably mounts relative to the distal end of housing 110 for protection of the contents of the cartridge 10 and optionally for protecting an injection needle which may be mounted at the distal end of the device.

Figure 2:
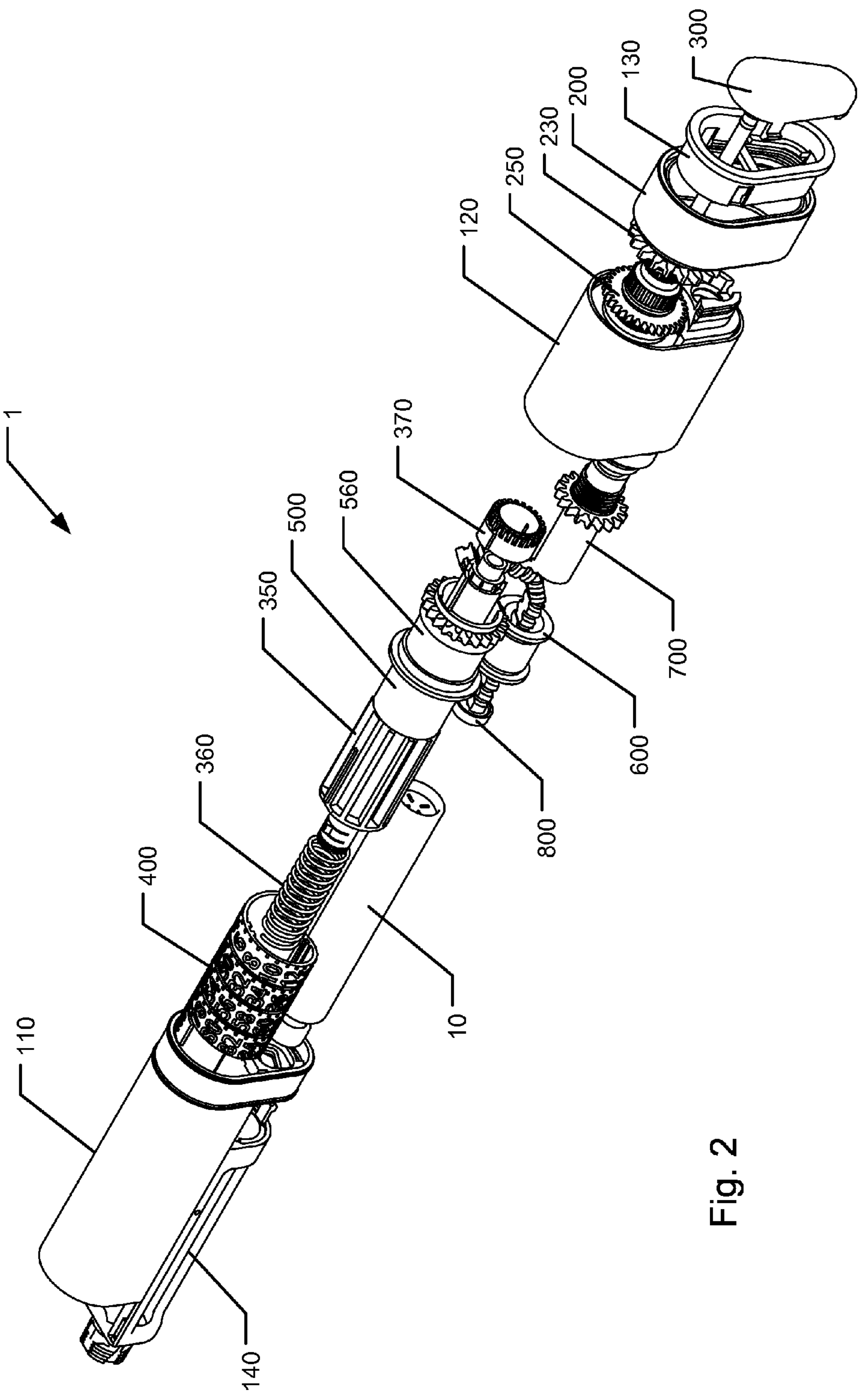
FIG. 2 shows an exploded perspective view of the main components of the injection device 1 of FIG. 1.
Figure 3:
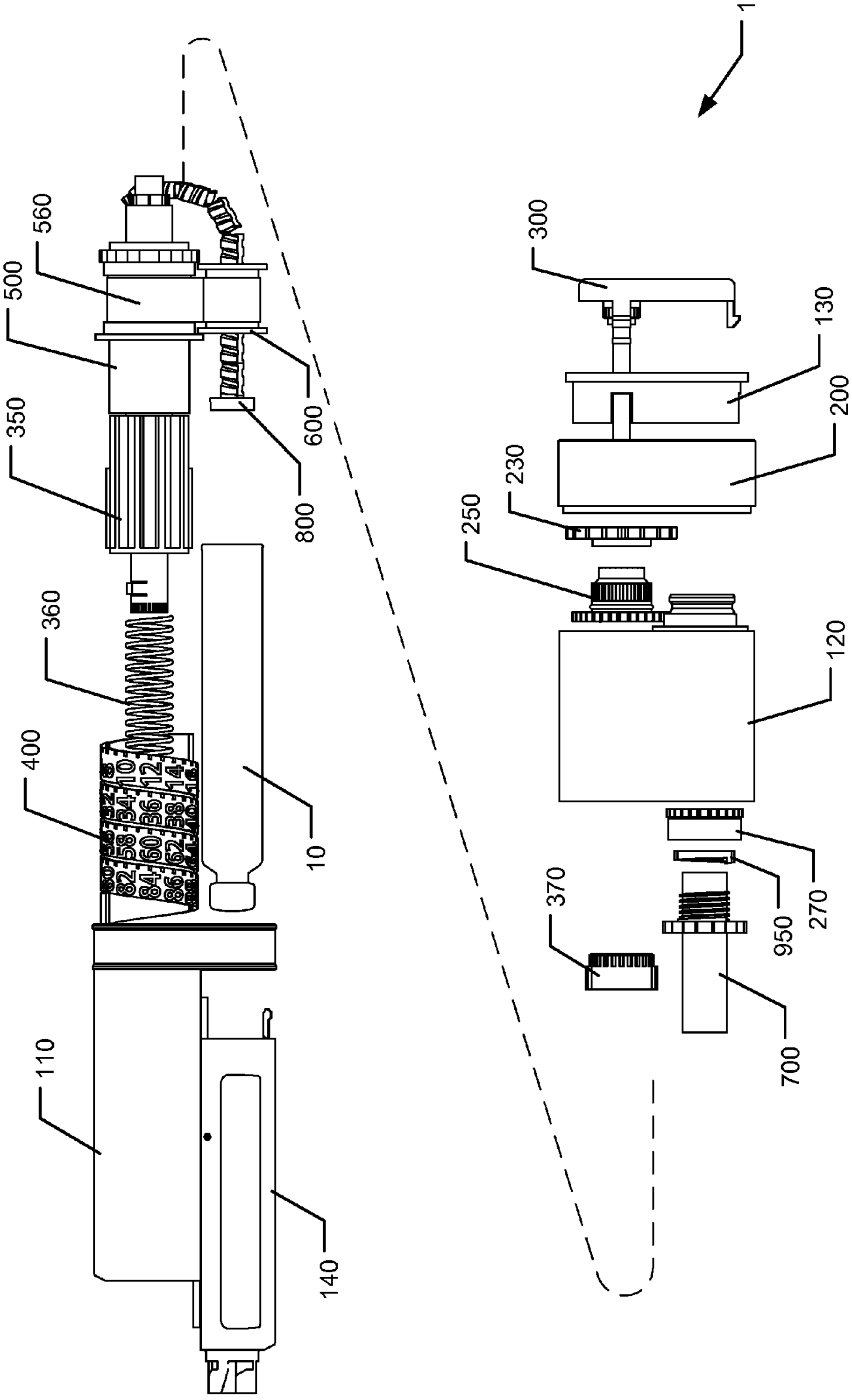
FIG. 3 shows an exploded sectional view of the main components of the injection device 1 of FIG. 1.

Referring to FIG. 1, the main components of the injection device 1 will now be described. FIG. 1 only includes references referring to the main components. Also exploded perspective and cross-sectional views of the main components of the injection device 1 are depicted on FIGS. 2 and 3. For further details to each of the components reference is made to the remaining figures, in particular FIGS. 4*a*-4*d*.

The housing (110,120,130,140) comprises a distal housing part 110, an intermediary housing part 120, a proximal housing part 130 and a cartridge housing part 140. Injection device 1 further comprises a dose injection mechanism operable by an injection activator in the form of an injection button 300 and a dose setting mechanism operable by a dosage selector 200.

The dose injection mechanism comprises a piston rod 800 that engages the piston 13 (by means of a piston washer). Piston rod 800 extends axially in the proximal direction away from piston 13. In the shown embodiment, the piston rod 800 is of a flexible type having a piston engaging end and a free end and wherein the flexibility is provided by forming the piston rod as a series of interconnected links. The flexibility allows the free end of the piston rod to be deflected away from the expelling axis. It is to be noted that FIG. 1 and FIGS. 4*a*-4*d* only show the most distal part of piston rod 800, the remaining parts of piston rod 800 is for clarity reasons omitted from these drawings. However, the structure of piston rod 800 is more clearly depicted in FIGS. 2 and 3 where it can be seen that, in the depicted operating state for the piston rod 800, the piston engaging end of the piston rod 800 assumes a straight portion whereas the free end assumes a bended portion.

In the shown embodiment, the piston rod 800 is a segmented type rod that consists of interconnected hinged rod elements that are adapted to swivel relative to each other at least in a particular direction of rotation so that the free end of the piston rod 800 may bend away from the expelling axis. When parts of the piston rod 800 assume a straight configuration, the rod elements are substantially incompressible so that the piston rod 800 is able to act as a push rod. Along its longitudinal extension piston rod 800 defines a first track and a second track each adapted to cooperate with a respective one of a nut member and a rotation control member so that relative rotation between the nut member and the rotational control member results in a longitudinal movement of piston rod 800. In alternative embodiments, the piston rod may be formed as a coiled axially incompressible spring which along its length is deflected away from its neutral rectilinear shape and that serves to transfer forces to the piston of the cartridge.

In the shown embodiment, the first track of the piston rod 800 defines an external thread (not referenced) and the second track (not referenced) defines a rotation control geometry that cooperates with a guide member 112 formed in distal housing part 110 to ensure that at least the straight portion of piston rod 800 is kept substantially in-rotatable. The rotation control geometry of the piston rod 800 may for example include one or more planar portions adapted to mate with a cooperating structure of the guide member 112 so as to prevent rotation between the piston rod 800 and the cooperating guide member 112.

As shown in FIG. 1, the dose injection mechanism of injection device 1 comprises a drive nut 700 having an internal thread 709 that engages the external thread of the piston rod 800. Drive nut 700 is mounted rotatably free but axially fixed relative to the housing so that drive nut 700 is able to rotate around the expelling axis, the amount of rotation of drive nut 700 thereby being decisive for the axial distal displacement of the straight portion of the piston engaging end of the piston rod 800.

In an alternative configuration of device 1 the drive nut would include a geometry which engages an axially extending track of the piston rod whereas the guide member would be threadedly engaged with a thread of the piston rod. A still further alternative is to use a piston rod with two separate threads having different thread leads where each respective thread is engaging a corresponding thread in the piston nut and the guide member. It is to be noted that in the context of the present application the term "drive nut" is means to cover all these variants of a drive nut.

The dose injection mechanism further includes a drive member 500 that is mounted rotatable but axially fixed relative to the housing, the drive member 500 being in rotational engagement with drive nut 700 so that the drive nut 700 rotates as the drive member 500 rotates. An actuator providing a stored energy source exerts a substantially constant driving force on drive member 500 in the particular direction of rotation that enables the piston rod 800 to be driven in the distal direction. In the shown embodiment, the stored energy source comprises a drive spring 560 in the form of a flat spiral spring that initially is stored on a storage drum 600 and which spools onto the drive member 500 as the energy accumulated in the drive spring 560 is released for driving the piston rod 800 in the distal direction. As regards further details of the drive mechanism reference is made to the discussion further below in relation to FIGS. 10 and 11.

As noted above, injection device 1 further includes a dose setting mechanism allowing a user to set a desired dose to be injected by means of the dose injection mechanism.

Coupled to the dose setting mechanism and the dose injection mechanism is a clutch mechanism that ensures that during dose setting, no movement of the drive mechanism is possible and that ensures that during dose injection the dose setting cannot be manipulated to alter a dose setting that has previously been set. Hence the clutch mechanism defines the injection device 1 to be operated in a dose setting mode and in a dose expelling mode. In the shown embodiment the clutch mechanism includes 4 separate clutch arrangement mechanisms. In FIGS. 4*a*-4*d* and in the following discussion these four clutch arrangement mechanisms are respectively designated a first, a second, a third and a fourth clutch arrangement (C1, C2, C3, C4).

The injection button 300 is arranged to protrude in a proximal direction from the proximal housing part 130 and arranged for limited axial movement between a default proximal position and a distal pressed down position. The mode of the clutch mechanism is controlled by the injection button 300. When the injection button 300 is depressed into the distal position the injection device 1 is in dose expelling mode whereas when the injection button 300 assumes its default proximal position the injection device 1 is in dose setting mode. The injection button 300 is arranged relative to the housing of the device 1 so that the injection button 300 cannot rotate.

The clutch mechanism includes a drive clutch 370 mounted between the drive member 500 and the housing part 120 that controls whether or not drive member 500 is allowed to rotate relative to the housing. The clutch mechanism will be described in greater detail further below.

The dose setting mechanism comprises a dose setting member 250 that is manually operable by turning dosage selector 200. Dose setting member 250 is axially fixed relative to the housing but rotates around an axis defining a dose setting axis that extends in parallel with the expelling axis but is separated from the expelling axis by a certain distance. A dosage selector connector 230 couples movement of dosage selector 200 with rotation of the dose setting member 250 so that the dose setting member 250 may be rotated in either direction controlled by movement of the dosage selector 200. Between dosage selector connector 230 and dose setting member 250, a slip coupling may be arranged to prevent destruction on the mechanism in case excessive forces are being applied on dosage selector 200. In the shown embodiment, as more clearly indicated on FIG. 2, dosage selector 200 is arranged along a cross section transverse to the expelling axis that runs through the housing i.e. between intermediary housing part 120 and proximal housing part 130. Dosage selector is formed as an endless flexible band 200 that generally conforms to the shape of the exterior surfaces of housing parts 120 and 130 due to the engagement with guiding structures formed in housing parts 120 and 130. Hence, the flexible band 200 may be moved along the directions of circumference of the flexible band in a first direction to increase the setting of a dose and in the opposite direction for decreasing an already set dose. An interior surface of the flexible band 200 forms a series of teeth that cooperate with dosage selector connector 230 to transform movement of flexible band 200 into a rotation of dose setting member 250. In other embodiments, instead of a flexible band 200 the dosage selector may be provided as a wheel or knob that may be manually turned for operating the dose setting mechanism. The dosage selector may for example be formed by dose setting member 250 by arranging openings in the housing of the device suitable formed to allow manual manipulation of dose setting member 250.

Further, a dose control member 350 extends longitudinally along the dose setting axis. The dose control member 350 is arranged in the housing for limited axial movements between a proximal position and a distal position. A pin 310 of injection button 300 extends distally from injection button 300 along the dose setting axis and into an opening of dose control member 350. Pin 310 serves to couple axial movements of the injection button 300 with axial movements of dose control member 350 but allows the dose control member 350 to be rotated around the dose setting axis.

A compression spring 360 is arranged in the housing to exert a proximally directed force on the dose control member 350 to bias the dose control member 350 and hence the injection button 300 into the proximal (default) position.

Positioned coaxially with the dose control member 350 and in distal housing part 110 is a dose dial scale 400 arranged. In the shown embodiment, the dose dial scale 400 is provided as a tubular sleeve that defines an exterior thread 407 engaging an interior thread 117 formed in distal housing part 110 (see FIG. 4*a*). Along an exterior helical path, the dose dial scale 400 is provided with a series of numerals each referring to individually selectable doses of a drug that the injection device 1 is designed to set and to expel. Housing part 110 is provided with an opening or window (not shown) through which a current dose setting is viewable.

Dose dial scale 400 is adapted to rotate together with the dose control member 350 but dose dial scale 400 is movable in axial directions relative to dose control member 350. In the shown embodiment this function is facilitated by means of an interior surface of the dose dial scale 400 that defines one or more axially extending tracks 401 that cooperates with corresponding one or more axially extending tracks 351 formed on an exterior surface of the dose control member 350 (see FIGS. 4*a* and 11).

Dose dial scale 400 includes a minimum limiting stop surface and a maximum limiting stop surface that define two extreme end positions that dose dial scale may assume during operation of the injection device 1 preventing operation outside the two extreme end positions. As best viewed in FIG. 3, dose dial scale 400 includes said two stop surfaces as axially extending ledges (non-referenced) that each is adapted to cooperate with a respective dose stop surface defined by distal housing part 110 and intermediary housing part 120. In the shown embodiment, dose dial scale 400 is adapted to experience a total rotation of 3.5 turns relative to the housing between a zero dose position and a maximum dose position. In the shown embodiment the dose dial scale 400 is provided with 100 separate dose markings along a helical path.

Dose control member 350 serves several functions relating both to the dose setting mechanism and to the dose injection mechanism of injection device 1.

When the injection device 1 is in dose setting mode, i.e. when the injection button 300 is in the default proximal position, dose control member 350 couples a rotation of the dose setting member 250 with rotation of the dose dial scale 400.

When the injection device 1 is in dose expelling mode, i.e. when the injection button 300 is in the pushed down position, the dose control member 350 couples rotation of the drive member 500 with rotation of the dose dial scale 400.

Dose control member 350 further includes a resilient tooth 359 (see FIG. 4*a*) adapted to engage a series of axial splines 119 formed in the distal housing part 110. The resilient tooth 359 and the splines performs as a click mechanism that makes the dose setting occur in discrete steps, e.g. corresponding to the number of numerals provided on the dose dial scale 400. During dose setting, the injection device 1 hereby emits a series of clicks as the dosage selector 200 is manipulated. In addition, as a dose of drug is being expelled, the click mechanism emits a series of click sounds as the dose control member 350 is rotated, e.g. one click as each unit of doses being expelled. Due to the axial splines 119, the dose control member 350 is allowed to move axially without this having influence on the performance on the click mechanism.

Besides the above functions, also the function of the drive clutch 370 is coupled with movements of the dose control member 350. In addition an end of content mechanism (EOC) including an EOC track follower 900 is coupled to the movement of dose control member 350. As will be appreciated by a person skilled in the art, an end of content mechanism is a mechanism which prevents the setting of a dosage amount which exceeds the useable dose amount remaining in the drug cartridge, i.e. the amount remaining in the cartridge that can be expelled with the required accuracy.

The function of the drive clutch 370 is provided by means of a second clutch arrangement C2 (122, 372) between the drive member 500 and the intermediary housing part 120. Drive member 500 and drive clutch 370 are rotationally locked relative to each other so that they rotate together but drive clutch 370 may be moved slightly in the axial direction relative to the drive member 500. Between drive clutch 370 and dose control member 350 is a coupling which ensures that the axial movements of drive clutch 370 follows axial movements of the dose control member 350 but relative rotational movements between these two components are enabled. Drive clutch 370 includes a series of teeth 372 adapted to engage corresponding teeth 122 formed in the intermediary housing part 120 (see FIGS. 4*a*, 4*c* and 11). Hence, when the injection button is in the proximal position, the drive member 500 is locked relative to the housing so that rotation of drive member 500 is prevented. Upon depression of injection button 300, the drive member 500 is released from the rotational locking relative to the housing allowing the drive member 500 to rotate. Hence, only when the injection button is depressed the drive member 500 is allowed to rotate and an expelling operation may in this way be facilitated.

Figure 4A:
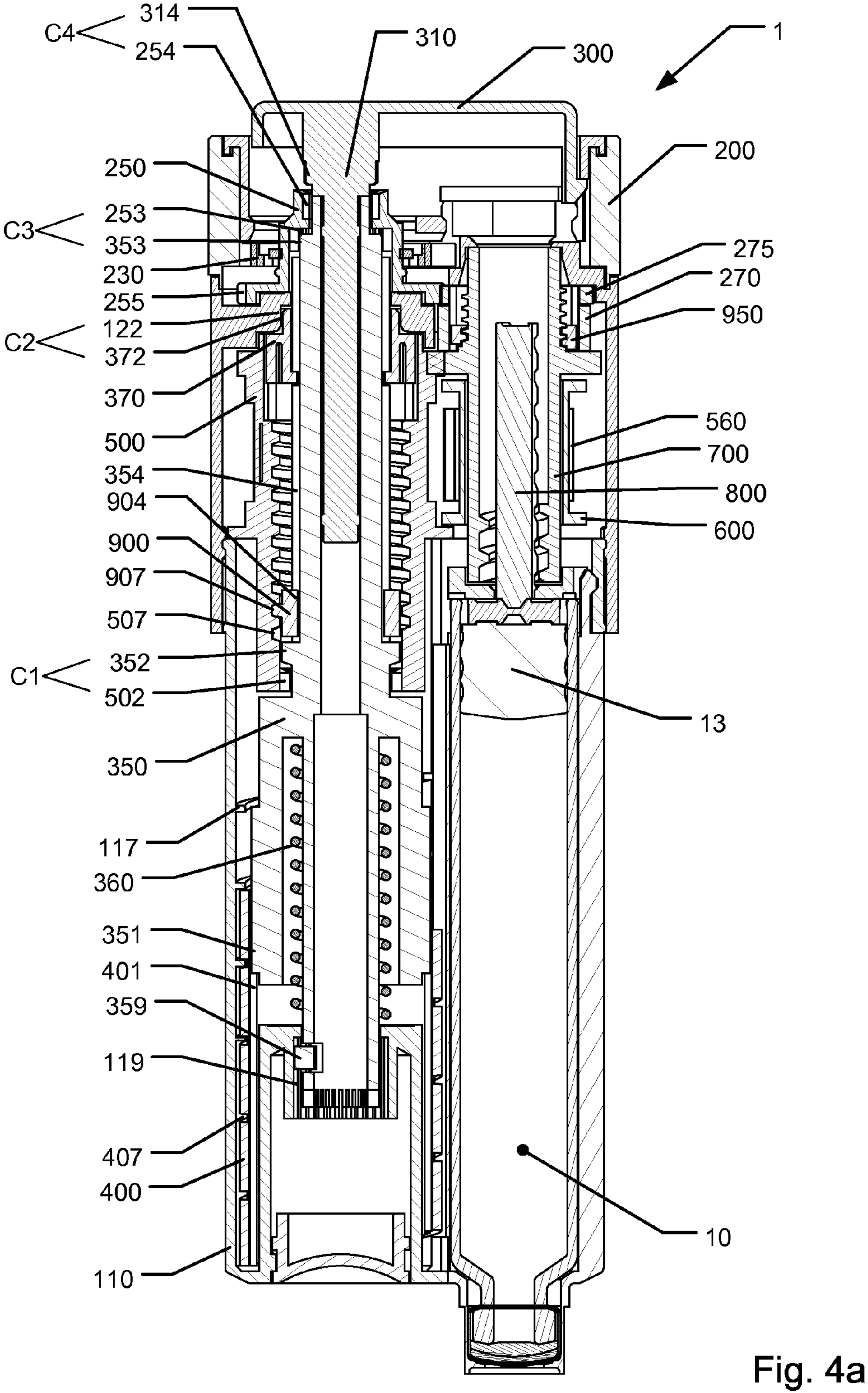
FIG. 4*a* is a cross sectional side view of the device of FIG. 1 in an initial state before the setting of a dose.
Figure 10:
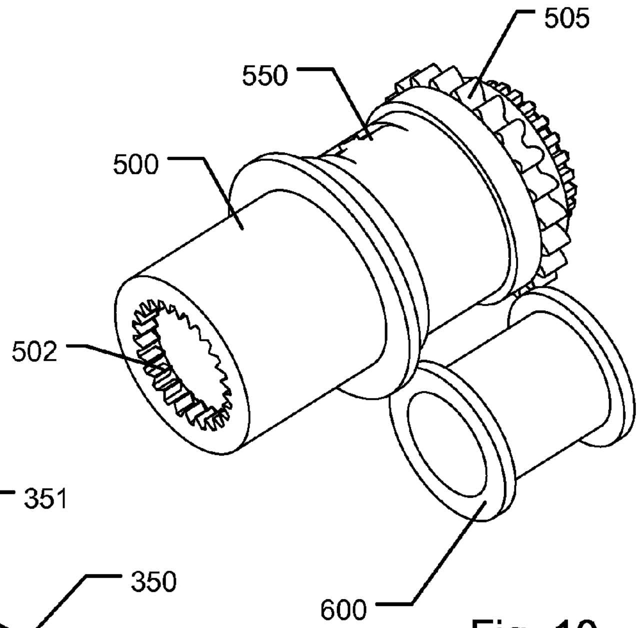
FIG. 10 is a perspective distal view of selected components of FIG. 5*b*.

A first clutch arrangement C1 (502, 352) is provided between the drive member 500 and the dose control member 350.The drive member 500 defines a distal circular opening along which a series of teeth 502 are arranged (see FIGS. 4*a* and 10). The dose control member 350 includes a series of corresponding teeth 352. When the dose control member 350 is in its distal position (see FIGS. 4*a* and 10), the teeth 352 of dose control member 350 engage with the teeth 502 of drive member 500 to effectively lock the two components against relative rotation. Hence when the injection button 300 is pushed down during dose injection, the rotation of the drive member 500 is coupled with rotation of dose control member 350. When the dose control member 350 is moved into its proximal position, the teeth 352 are moved out of engagement with the teeth 502 of drive member 500. Hence when the injection button 300 is released, rotation of the dose control member 350 relative to drive member 500 is enabled.

A third clutch arrangement C3 (253, 353) is provided between the dose setting member 250 and the dose control member 350. The proximal part of dose control member 350 includes a series of teeth 353 (see FIG. 4*a* and FIG. 11) that is adapted to engage corresponding teeth 253 formed in dose setting member 250 (see FIGS. 4*a*, 5*a* and 6). When the dose control member 350 is in its proximal position, the teeth 353 are adapted to slide into engagement with the teeth 253 of dose setting member 250. Hence, when the injection button 300 is in its released position, the rotation of dose setting member 250 during dose setting is coupled with rotation of the dose control member 350. When the dose control member 350 is in its distal position, the teeth 352 are moved out of engagement with the teeth 502 of drive member 500. Hence when the injection button 300 is pushed down, rotation of the dose control member 350 relative to dose setting member 250 is enabled.

A fourth clutch arrangement C4 (254, 314) is provided between the dose setting member 250 and the injection button 300. Dose setting member 250 defines a proximal circular opening along which a series of teeth 254 are arranged (see FIGS. 4*a*, 5*a* and 6). The distally extending pin 310 of injection button 300 includes a series of corresponding teeth 314 (see FIGS. 4*a* and 3). When the dose control member 350 is in its distal position (shown in FIG. 4*c*), the teeth 314 of injection button 300 engage with the teeth 254 of the dose setting member 250 to prevent relative rotation between the dose control member 350 and injection button 300. Hence, when the injection button 300 is pushed down during dose injection, rotation of the dose setting member 250 relative to the housing is prevented. In the disclosed embodiment the dosage selector 200 cannot be operated during dose injection. When the dose control member 350 is moved into its proximal position (shown in FIGS. 4*a*, 4*b* and 4*d*), the teeth 314 are moved out of engagement with the teeth 254 of the dose setting member 250. Hence, when the injection button 300 is released, rotation of the dose setting member 250 relative to the housing is enabled which allows for a dose to be set by operating dosage selector 200.

Figure 5A:
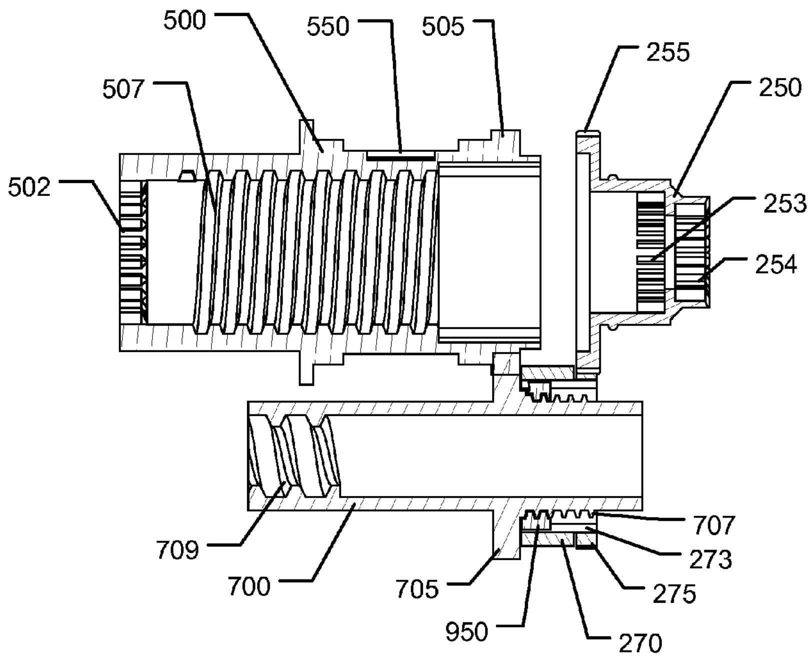
FIG. 5*a*, shows a cross sectional side view of components relating to the drive mechanism of the device shown in FIG. 1.
Figure 5B:
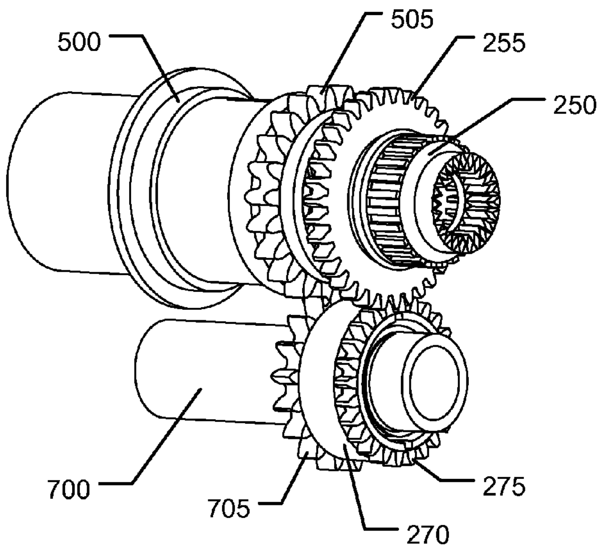
FIG. 5*b* is a perspective proximal view of the components shown in FIG. 5*a*.
Figure 6:
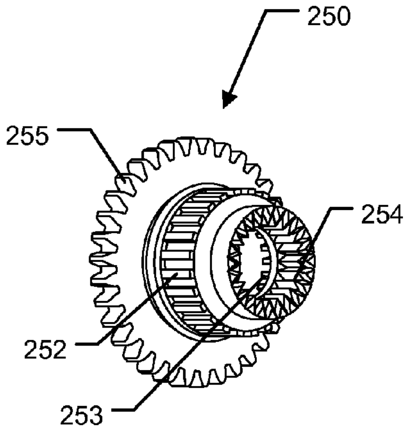
FIG. 6 is a perspective proximal view of a dose setting member 250 of the device shown in FIG. 1, FIGS. 7*a*, 7*b* and 7*c* depict detailed perspective views of components 700, 270 and 950 relating to a secondary stop limiter.

As shown in FIGS. 4*a*, 5*a* and 5*b* the drive member 500 includes a cylindrical section forming a gear wheel 505. Also the drive nut 700 includes a cylindrical section forming a gear wheel 705 that engages gear wheel 505. Hence a rotation of drive member 500 in a particular direction during dose injection is transferred to rotation in the opposite direction of drive nut 700.

Figure 11:
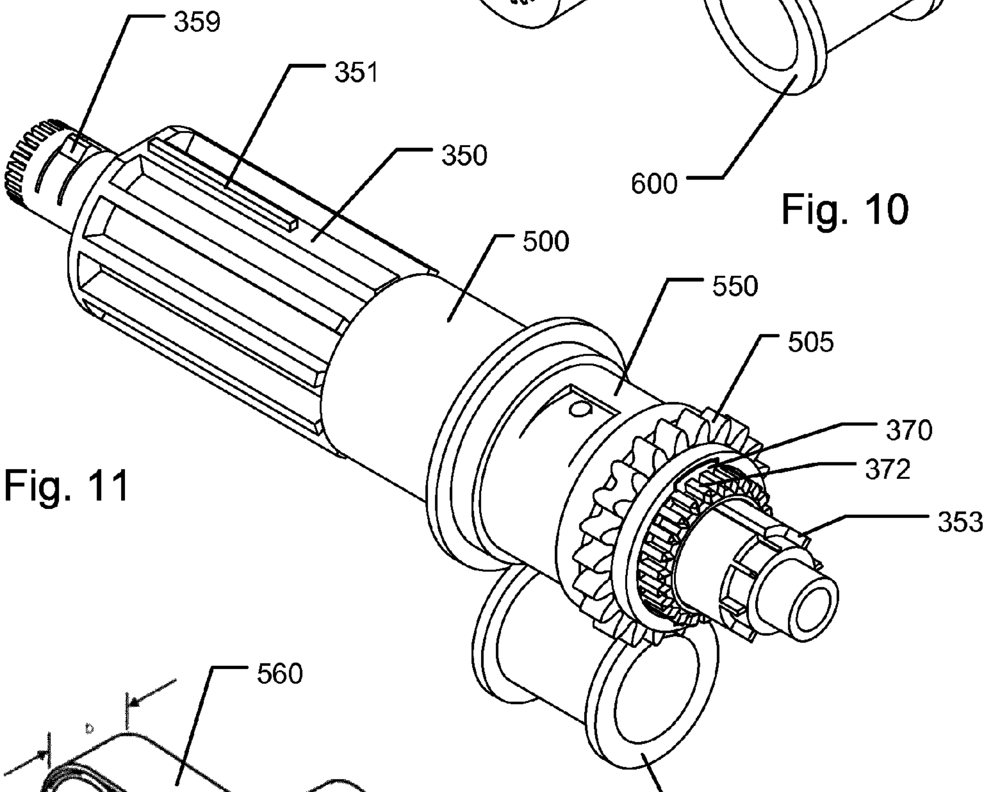
FIG. 11 is a perspective proximal view of selected components relating to the dose setting and driving mechanism of the injection device 1 of FIG. 1.

FIGS. 10 and 11 show perspective representations of selected components of the drive mechanism included in injection device 1.

Figure 12:
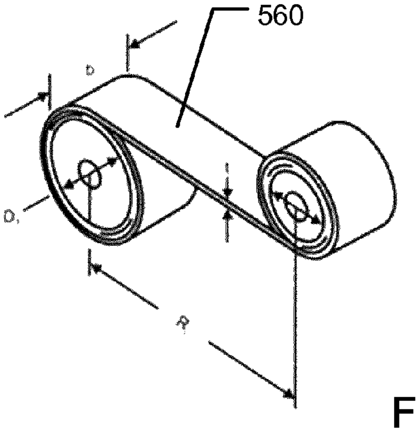
FIG. 12 is a schematic representation of the drive spring of the injection device 1 of FIG. 1.

The drive member 500 includes a further cylindrical spring receiving section 550 that is arranged to reside next to the storage drum 600 in the same axial position in the housing of the device as the storage drum 600. Drive nut 700 provides a bearing surface adapted to receive storage drum 600 so that storage drum may rotate independently relative to the drive nut 700. In this embodiment, the drive spring 560 is provided as a constant force spring arranged between the storage drum 600 and the cylindrical spring receiving section 550 of drive member 500. The spring 560 may be arranged to constitute an S-shaped curve in a manner schematically shown on FIG. 12. The drive spring 560 may be adapted to have a natural tendency to reside on the storage drum 600. However, during production of the injection device 1 the drive spring 560 is forced onto the cylindrical spring receiving section 550 thereby accumulating energy in drive spring 560. Upon release, the accumulated energy of the drive spring 560 urges drive member 500 to rotate while the drive spring 560 gradually winds up onto storage drum 600. The cylindrical spring receiving section 550 includes means (non-referenced) to fasten the end of the drive spring 560 so that slippage between the drive spring 560 and drive member 500 will not occur.

In other embodiments, the direction of movement may be reversed so that the drive spring 560 may gradually seek to move onto the drive member 500 during energy release, i.e. during dose expelling. Also other configurations of drive springs than the shown S-type spring may be used.

In the shown embodiment, the drive spring 560 is fully loaded during the assembly of the injection device 1. When purchased by the user, the drive spring contains sufficient energy to deliver the entire useable amount of drug contained in the cartridge 10.

During dose setting, the dose control member 350 is rotated in accordance with the dose set as adjusted by means of dosage selector 200. This has the effect that the dose dial scale 400 is rotated away from its zero dose position. The amount of rotation of dose dial scale 400 therefore exactly corresponds to the selected dose size. During this movement the first clutch arrangement is in the released state so that the drive member 500 is not being operated. It is noted that during dose setting, the second clutch arrangement C2 is engaged meaning that the drive member 500 is prevented from rotating.

The dose setting may be performed by dialling up and down dosage selector 200 until a desired dose shows up in the dose window of the housing. After the desired dose has been dialled, and after an injection needle has been mounted relative to the drug cartridge 10, the desired dose is ready for injection.

After applying a suitable force on the injection button 300 to press down the injection button to the distal position (see FIG. 4*c*), the first clutch arrangement C1 is in the engaged state and the second clutch arrangement C2 is in the released state. Hence, the drive member 500 is released for rotation relative to the housing and is urged by spring drive 560 to rotate thereby carrying with it the dose control member 350. As long as the injection button 300 is maintained in the depressed position, the drive member 500, the dose control member 350 and the dose dial scale 400 rotates together towards the zero dose position. All this time the drive nut 700 rotates to drive forward the piston rod 800 resulting in the expelling of the drug through the attached needle. The movement is stopped when the minimum limiting stop surface of the dose dial scale 400 engages the corresponding dose stop surface formed in distal housing part 110. This simultaneously stops the drive member 500 from rotating and the piston rod 800 will move no further.

It is to be noted that during dose injection procedure, the expelling may be halted at any time by releasing the finger pressure exerted on the injection button 300. When pressure is released the dose control member 350 is automatically moved into its proximal position due to the bias provided by compression spring 360, Hence, clutch arrangement C2 re-engages which thus prevents the drive member 500 from rotating. However, expelling of the remaining part of the set dose may be continued by renewed pressing down the injection button 300.

Hence the dose dial scale 400 acts as a metering device during dose setting where the return movement of the dose dial scale 400 during injection determines the amount that will be expelled. In this way the dose dial scale provides a primary stop limiter.

The injection device 1 further includes a secondary stop limiter which performs as a safety back up function in case that a mechanical error occurs somewhere in the dose setting mechanism or somewhere in the dose injection mechanism. In the shown embodiment, the drive nut 700 is associated with such a secondary stop limiter. As apparent from FIGS. 1 and in particular FIGS. 5*a*-5*b*, 7*a*-7*c*, 8 and 9 the secondary stop limiter includes the said drive nut 700, a secondary stop ring 270 arranged coaxially with the drive nut 700 and a secondary stop track follower 950 arranged between the drive nut 700 and secondary stop ring 270.

Figure 7A:
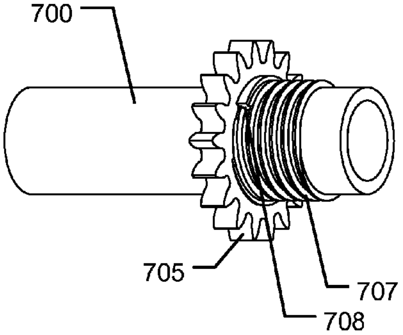

As shown in FIG. 7*a*, the drive nut 700 includes an external thread 707 provided on a proximal cylindrical portion thereof. The drive nut 700 defines a stop surface 708 located at a particular position relative to the thread 707.

Figure 7B:
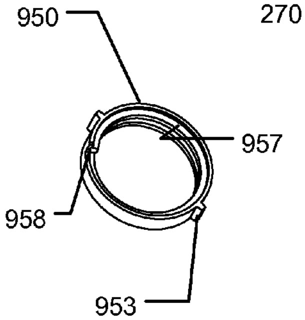

Referring to FIG. 7*b*, the secondary stop track follower 950 is in this embodiment in the form of a cylindrical nut that defines an internal thread 957 adapted to engage the thread 707 of drive nut 700. The secondary stop track follower 950 defines a stop surface 958 that is adapted to engage the stop surface 708 provided on drive nut 700 for a particular relative rotational and axial position between the secondary stop track follower 950 and drive nut 700. The secondary stop track follower 950 further comprises one or more track elements 953 extending radially outwards from an outer cylindrical surface of secondary stop track follower 950.

Figure 7C:
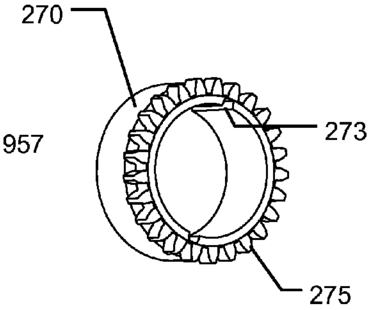

As shown in FIG. 7*c*, the secondary stop ring 270 is a generally cylindrical sleeve that includes a cylindrical bearing surface (non-referenced) adapted to be rotatably supported in the housing at a fixed location thereof. An interior surface of the stop ring 270 includes one or more axially extending tracks 273 each of which is adapted to cooperate with respective ones of track elements 953 of the secondary stop track follower 950. In this way the secondary stop track follower 950 is configured to rotate with the secondary stop ring 270 but allows relative axial displacement of secondary stop track follower 950 relative to secondary stop ring 270. A cylindrical section of secondary stop ring 270 forms a gear wheel 275 that is adapted to engage the gear wheel 255 section of dose setting member 250.

Figure 8:
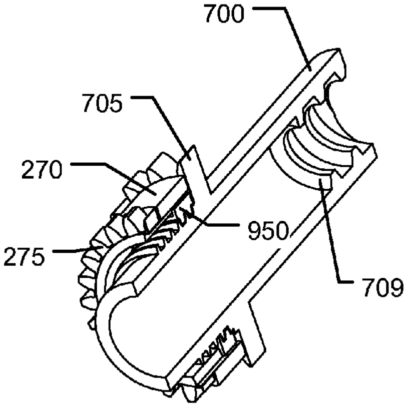
FIG. 8 shows a perspective cross sectional view of the components of FIGS. 7*a*, 7*b* and 7*c* in an assembled state.
Figure 9:
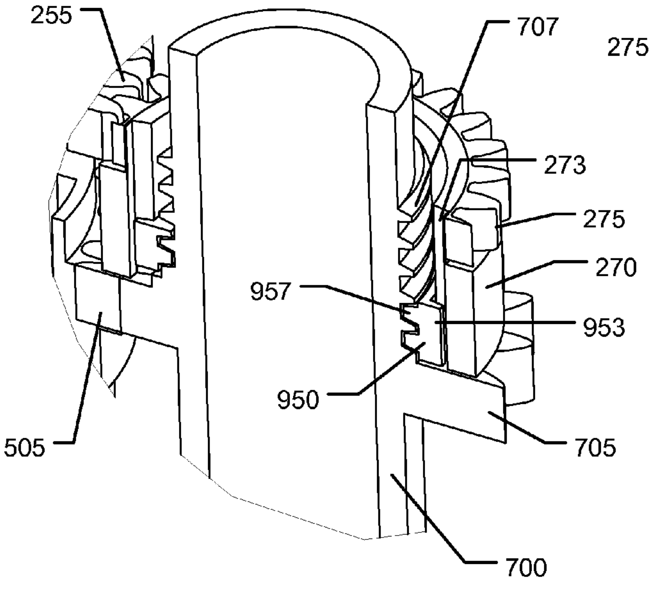
FIG. 9 shows a perspective cross sectional partial view of components shown in FIG. 5*b*.

In the assembled state the drive nut 700, the secondary stop ring 270 and the secondary stop track follower 950 forms an assembly that more easily is viewed in FIGS. 5*a*, 8 and 9.

Due to the threaded engagement between the secondary stop track follower 950 and the drive nut 700, the secondary stop track follower 950 will be moved back and forth in the axial direction as the secondary stop track follower 950 and the drive nut 700 rotate relative to each other.

Before the setting of a dose, when the dose dial scale 400 indicates the zero dose setting through the window in the housing, the secondary stop track follower 950 will assume an initial position relative to the drive nut 700. In this state the stop surface 958 of the secondary stop track follower 950 will be situated in close proximity with respect to the stop surface 708 provided on drive nut 700. As a dose is dialled up by manipulating dosage selector 200 the dose setting member 250 will be rotated and, due to the engagement between gear wheel 255 and gear wheel 275, the secondary stop ring 270 and the secondary stop track follower 950 will be rotated as well. As the drive nut 700 is maintained non-rotatable during dose setting, due to the threaded connection 707 and 957, the secondary stop track follower 950 will be moved in the proximal direction so that the stop surface 958 of the secondary stop track follower 950 will be moved further away from the stop surface 708 provided on drive nut 700.

During dose injection, when the injection button 300 is pressed down, the dose setting member 250 is prevented from rotating and hence the secondary stop ring 270 and the secondary stop track follower 950 are prevented from rotating as well. However, as the drive nut 700 rotates during injection, due to the threaded connection 707 and 957, the secondary stop track follower 950 will be moved in the distal direction.

In a correctly working injection device 1, upon reaching the end of dose state where the dose dial scale 400 is located so that its minimum limiting surface engages the corresponding dose stop surface defined by the distal housing part 110 (corresponding to the zero dose position), the secondary stop track follower 950 will be moved to assume the initial position as referred to above. In this position the stop surface 958 of the secondary stop track follower 950 will again be situated in close proximity with respect to the stop surface 708 provided on drive nut 700.

In case a mechanical failure occurs in the injection device, such as a failing primary stop limiter, a failing clutch arrangement C1 or a failing clutch arrangement C2, the biasing force exerted by the drive spring 560 on drive member 500 may cause the drive member to run freely causing the drive nut 700 to rotate and the piston rod 800 to move in the distal direction in an uncontrolled manner. However should such a situation arise, the drive nut 700 may slightly rotate but soon the secondary stop limiter will prevent further rotation of drive nut 700 as the stop surface 958 of the secondary stop track follower 950 will be in abutment with the stop surface 708 provided on drive nut 700.

In the shown embodiment, the drive nut 700 defines a thread 707 whereas the stop ring 270 defines one or more axially extending tracks 273 where the thread 707 and the tracks 273 engage corresponding structures on the secondary stop track follower 950. A similar function may be obtained by rearranging the thread to be disposed on the stop ring 270 and the axially extending tracks to be disposed on the drive nut 700 and rearranging the structures on the secondary stop track follower 950 accordingly. In still other embodiments, the secondary stop track follower 950 defines two threaded sections where each of the threaded sections operate with corresponding threads formed on the drive nut 700 and the stop ring 270 respectively. In such embodiment, the two threaded engagements are provided with threads of different lead so that the secondary stop track follower 950 is forced to move axially as the drive nut 700 and the stop ring 270 rotate relative to each other.

In the shown embodiment, the secondary stop track follower 950 is formed as a cylindrical nut. In alternative embodiments, the secondary stop track follower 950 may alternatively be provided as a half-nut or forming another structure such as ball clamped between tracks formed in the drive nut 700 and the stop ring 270 where the tracks have different lead.

The above mentioned end of content (EOC) mechanism will now be more fully described referring generally to FIG. 4*a*. In the shown embodiment, the dose control member 350 includes one or more longitudinal extending ribs 354 provided along an exterior cylindrical surface thereof. The drive member 500 includes an interior cylindrical surface that defines an interior thread 507. And end of content track follower (EOC track follower) 900 is formed as a cylindrical nut and arranged coaxially with the drive member 500 and the dose control member 350 so that the EOC track follower is located between the drive member 500 and the dose control member 350. The EOC track follower 900 defines an external thread 907 that cooperates with internal thread 507 of drive member 500. EOC track follower 900 further defines one or more internal axial recesses each adapted to cooperate with the one or more longitudinal extending ribs 354 of dose control member 350.

A not shown EOC limitation stop is associated with a proximal part of the thread 507 of drive member 500. In a known manner such stop may define a rotational stop surface adapted to engage a rotational stop surface (not shown) of the EOC track follower 900 for a particular relative axial and rotational position between the EOC track follower 900 and the drive member 500. The said EOC limitation stop limits the movement of the EOC track follower 900 in the proximal direction so that the settable size of the dose is limited to dosage amounts to which a corresponding dosage remains in the cartridge 10. In this way the dosage selector 200 cannot dial up a dose that is larger than the remaining useable dose accommodated in the cartridge.

Prior to use of the injection device, where the cartridge 10 is full and the piston rod 800 is located in the position shown on FIG. 4*a*, the EOC track follower 900 is positioned in an initial axial position relative to the housing (see FIG. 4*a*). During dialling up a dose the EOC track follower 900 is rotated as the dose control member 350 rotates relative to the drive member 500. Due to the threaded engagement 507, 907, the EOC track follower is moved in the proximal direction as a dose is dialled up (see FIG. 4*b*). Should the dosage selector 200 be moved for dialling down a previously set dose, the EOC track follower 900 will move in the distal direction in accordance with the reduction in dose size.

When an injection is initiated, the dose control member 350 will move to its distal position. This has no influence on the axial position of the EOC track follower 900. During injection wherein the first clutch arrangement C1 is in the engaged state, the dose control member 350 rotates along with the drive member 500. Hence, during this procedure, the EOC track follower 900 will retain its position relative to the thread 507 defined by the drive member 500 (see FIG. 4*c*).

Finally, after the dose injection has been completed, the injection button 300 is released and the first clutch arrangement C1 is disengaged and the second clutch arrangement C2 is engaged. Again, this has no influence on the axial position of the EOC track follower 900 (see FIG. 4*d*).

After additional subsequent dose setting and dose injection procedures the EOC track follower will move gradually in the proximal direction in accordance with the accumulated dialling up procedures during each of the performed administrations. As noted above, at a predetermined point the ECO track follower will abut an EOC limitation stop which will prevent further dialling up. Hereby the user is notified that the cartridge does not contain sufficient doses above a certain limit.

Figure 4B:
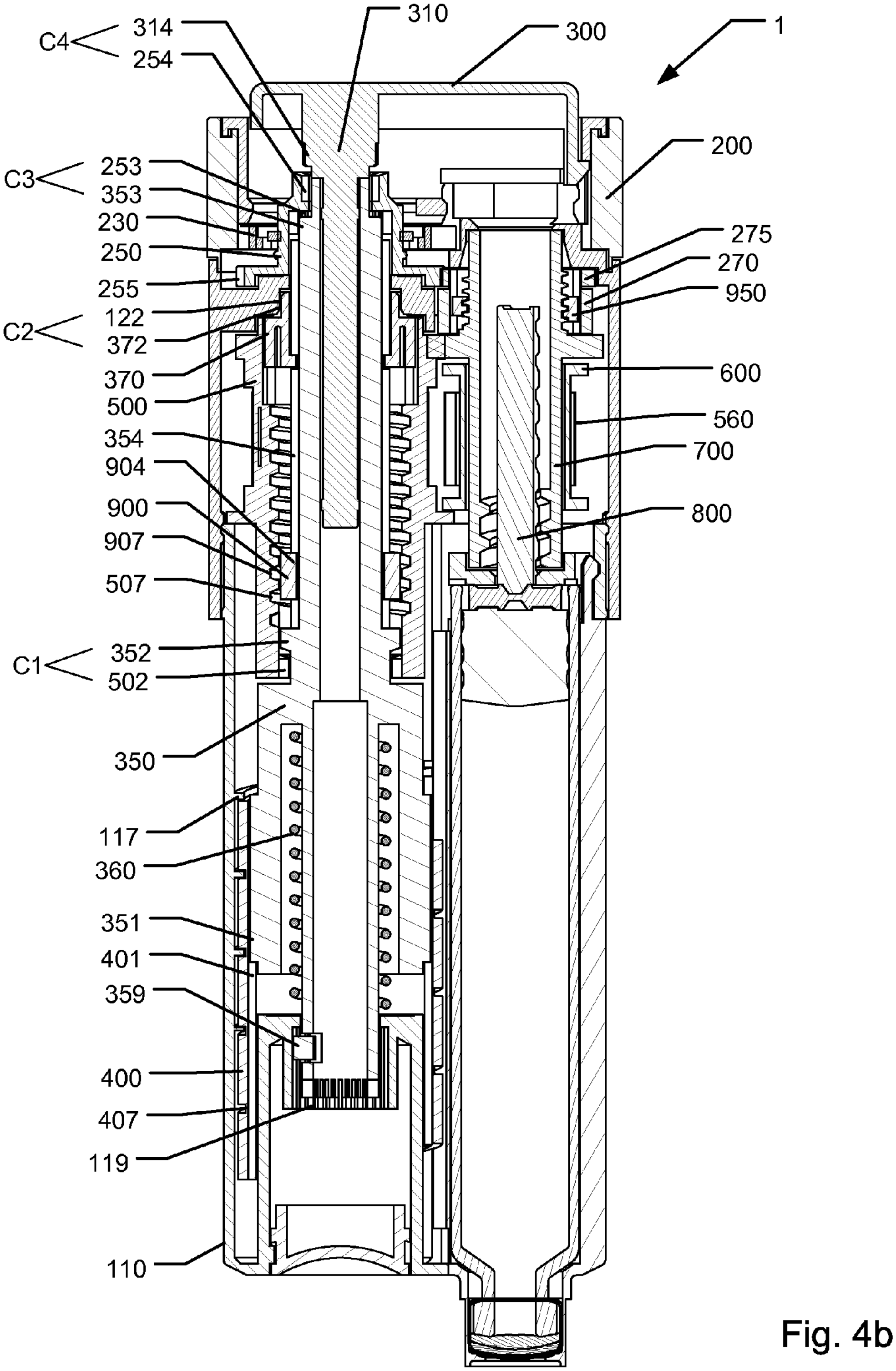
FIG. 4*b* is a cross sectional side view of the device of FIG. 1 where a dosage selector 200 has been operated to set a particular size of a dose.
Figure 4C:
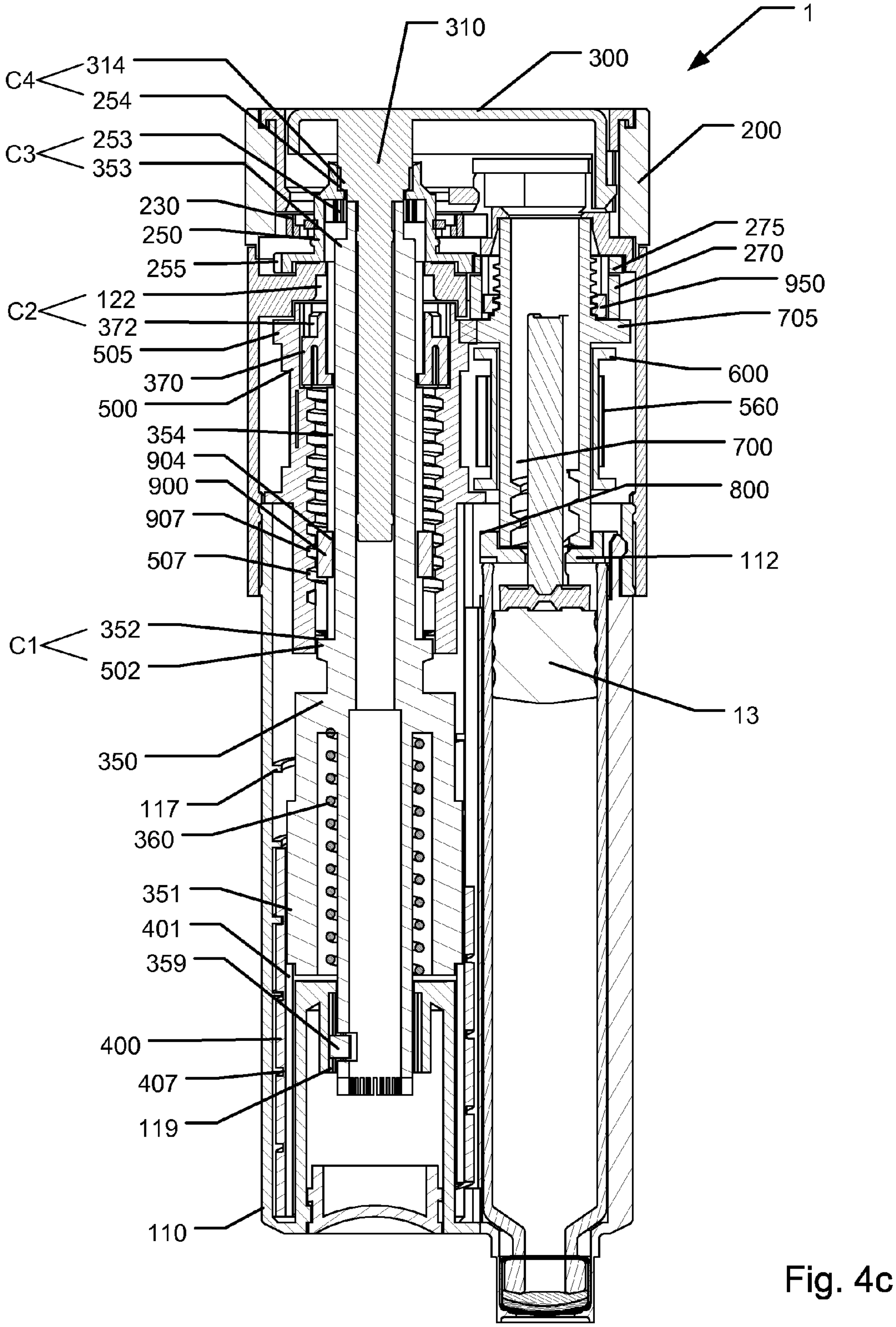
FIG. 4*c* is a cross sectional side view of the device of FIG. 1 where an injection button 300 has been pushed down and where the injection of the set dose has been completed.
Figure 4D:
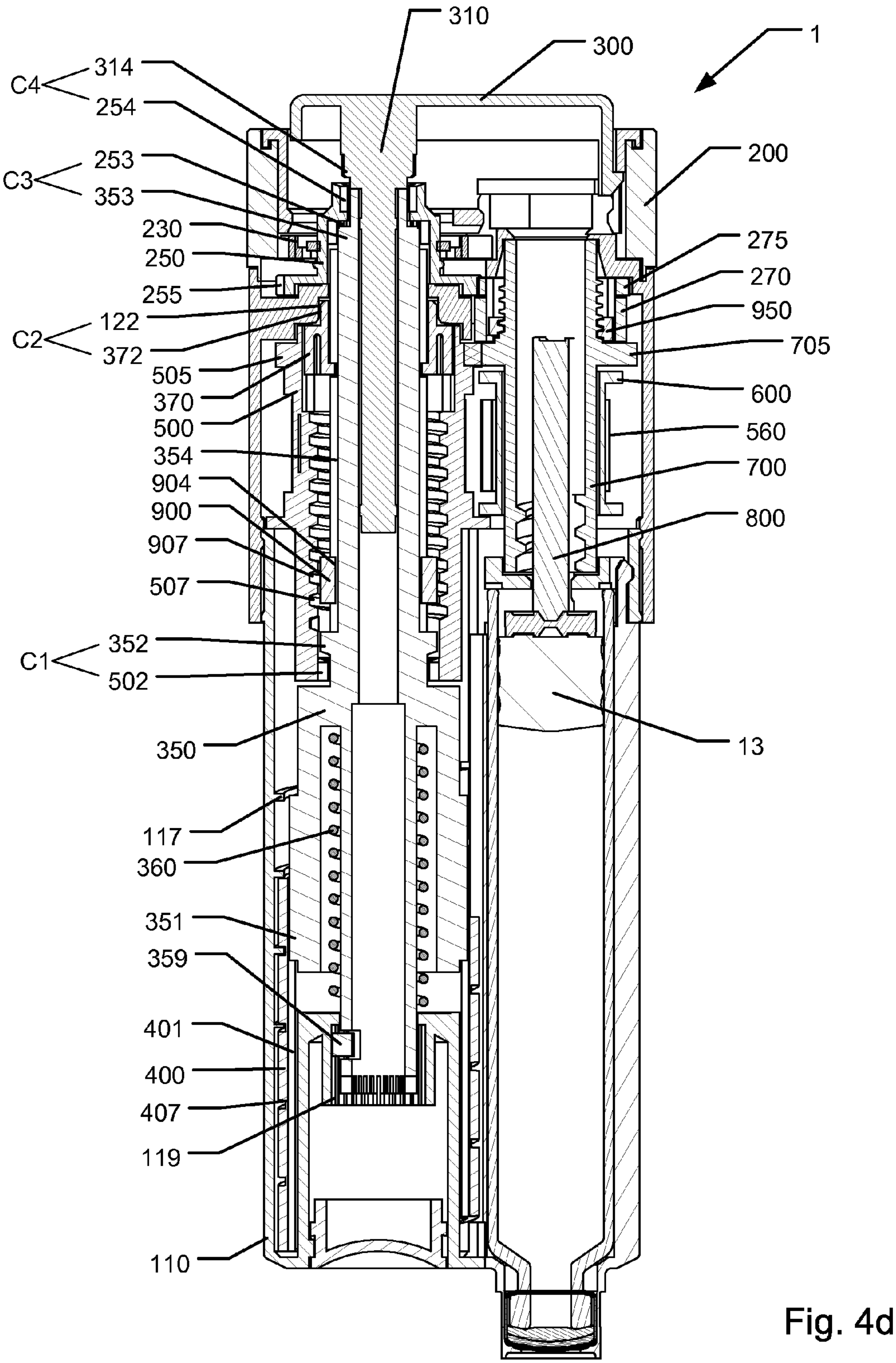
FIG. 4*d* is a cross sectional side view of the device of FIG. 1 after the completion of the injection of the set dose and wherein the injection button has been released.

As noted above the FIG. 4*a* shows the device in an initial state before the setting of a dose, FIG. 4*b* shows the device in a state where the dosage selector 200 has been operated to set a particular size of a dose, FIG. 4*c* shows the device in a state where the injection button 300 has been pushed down and where the injection of the set dose has been completed and, finally, FIG. 4*d* shows the device in a state after completion of the injection of the set dose and where the injection button 300 has been released.

By comparing the states shown in FIGS. 4*a*, 4*b*, 4*c* and 4*d*, the movement of each of the clutch arrangements C1, C2, C3 and C4 will become evident. Also, in accordance with the above description, the particular movements of the EOC mechanism and the secondary stop limiter providing the safety mechanism will become evident.

In the embodiment shown in the figures, the injection device defines a pre-filled injection device where a drug filled cartridge is arranged irremovably within the device. Subsequent to expelling the entire useable contents of the cartridge the pre-filled injection device is intended to be disposed of and, optionally, be replaced by a new disposable device. However, in other embodiments being slightly modified, the injection device may be adapted to be used as a device of the durable kind, wherein a first cartridge is replaced by a new one when the first cartridge has been emptied.

In line with the invention as set forth above, the invention is generally applicable to medical delivery devices, regardless of the kind of administration route for delivering a beneficial agent to the user. Also, the invention may be implemented in both manual injectors where the user directly delivers the necessary mechanical energy during the delivery process as well as spring assisted injectors where a pre-stressed or user strained spring in part or fully delivers the necessary mechanical energy during the delivery process. Further, the invention may be used in connection with other medical injection devices where actuators having other energy sources than spring actuators are used, such as pneumatically operated actuators having a pneumatic storage, prime mover actuators having an electrochemical cell storage or even electrical actuators having an electrical accumulator storage.

In the above description of the exemplary embodiments, the different structures providing the desired relations between the different components just as the means providing the described functionality for the different components have been described to a degree to which the concept of the present invention will be apparent to the skilled reader. The detailed construction and specification for the different structures are considered the object of a normal design procedure performed by the skilled person along the lines set out in the present specification.

The invention claimed is:

1. A medical injection device for setting and injecting set doses from a held drug cartridge, comprising:

a housing defining proximal and distal ends, a dose setting arrangement including a dose setting device that is moved in a first direction away from a predetermined primary stop in accordance with the size of a set dose and that moves back to the predetermined primary stop during injection of the set dose, the predetermined primary stop being configured for being fixedly arranged relative to the housing, a piston rod adapted to translate relative to the housing in a distal direction in order to expel a set dose, a driver coupled to the piston rod, the driver being adapted to rotate during dose injection to cause the piston rod to translate relative to the housing, and a mechanism adapted for coupling rotational movement of the dose setting device with rotational movement of the driver such that the driver exclusively rotates when the dose setting device moves back towards the predetermined stop during injection of the set dose, wherein the injection device further defines:

a secondary stop comprising:

a first component that rotates around a first axis as the driver rotates during injection but remains rotationally fixed relative to the housing during dose setting, the first component having a first track disposed thereon, a second component that is arranged coaxially with the first component for rotation around the first axis, wherein the second component rotates as the dose setting device rotates during dose setting and wherein the second component is rotatably fixed relative to the housing during dose injection, the second component having a second track disposed thereon, and a secondary stop track follower arranged between the first component and the second component, the secondary stop track follower being in engagement with the first track and in engagement with the second track, wherein the first track and the second track are configured to cause the secondary stop track follower to move along the first axis when the first component and the second component rotate relative to each other, and wherein, if the predetermined primary stop fails to stop the driver at the end of injection, the secondary stop track follower moves towards a safety stop to prevent the driver from rotating further.

2. An injection device as defined in claim 1, wherein one of the first track and the second track forms a thread and wherein the other one of the first track and the second track forms an axial track.

3. An injection device as defined in claim 1, wherein both the first track and second track form threads and wherein the lead of the first track is different than the lead of the second track.

4. An injection device as defined in claim 1, wherein at least one of the first track and the second track forms a thread and wherein the safety stop is arranged fixedly relative to the at least one thread.

5. An injection device as defined in claim 1, wherein the secondary stop track follower does not engage the piston rod.

6. An injection device as defined in claim 1, wherein the first component is the driver.

7. An injection device as defined in claim 1, wherein the safety stop forms a rotational stop surface adapted to abut a rotational stop surface provided on the secondary stop track follower to prevent further rotation of the first component beyond the safety stop.

8. An injection device as defined in claim 1, wherein the injection device includes a dosage selector coupled to the dose setting device for operating the dose setting device and an injection activator adapted to be activated to inject the set dose.

9. An injection device as defined in claim 1, wherein the injection device defines a first clutch arrangement arranged between the dose setting device and the second component, wherein the first clutch arrangement is engaged during dose setting so that the second component rotates as the dose setting device rotates, and wherein the first clutch arrangement is disengaged during dose injection to enable the dose setting device to rotate independently of the second component.

10. An injection device as defined in claim 9, wherein the injection device defines a second clutch arrangement arranged between the first component and the housing, wherein the second clutch arrangement is engaged during dose setting so that the first component is prevented from rotating during dose setting, and wherein the second clutch arrangement is disengaged during dose injection to enable the first component to rotate relative to the housing.

11. An injection device as defined in claim 1, wherein the injection device further comprises a stored energy source, the stored energy source being configured to drive rotation of the driver when the injection activator is activated.

12. An injection device as defined in claim 11, wherein the stored energy source comprises energy sufficient to drive the piston rod for expelling the entire useable contents of the cartridge.

13. An injection device as defined in claim 1, wherein at least a piston engaging end of the piston rod extends along the first axis, wherein the driver defines a drive nut that rotates around the first axis and wherein the dose setting device is adapted to rotate around a second axis, the second axis being offset from the first axis by a distance and wherein the driver further defines a drive member rotatable around the second axis, the drive member being coupled to the drive nut so that the drive nut rotates as the drive member rotates.

14. An injection device as defined in claim 1, wherein the piston rod is a flexible piston rod having a first end extending in parallel with the first axis and adapted to engage a piston of a held cartridge and wherein the second end of the piston rod is adapted to be flexed away from the first axis.

15. An injection device as defined in claim 1, wherein the longitudinal axis of a held cartridge defines a second axis, the second axis being offset from the first axis by a distance, wherein the driver defines a drive nut that rotates around the second axis and wherein the driver further defines a drive member rotatable around the first axis, the drive member being coupled to the drive nut so that the drive nut rotates as the drive member rotates wherein the dose setting device is adapted to rotate around the first axis, and wherein said first component is a component that rotates as the drive member rotates.

* * * * *